United States Patent [19]

Lund et al.

[11] Patent Number: 4,908,774
[45] Date of Patent: Mar. 13, 1990

[54] SYSTEM FOR ULTRASONIC EXAMINATION

[75] Inventors: Svend A. Lund, Birkerod; Willy D. Kristensen, Lyngby, both of Denmark

[73] Assignee: Akademiet for De Tekniske Videnskaber, Svejsecentralen, Denmark

[21] Appl. No.: 138,034
[22] PCT Filed: May 5, 1986
[86] PCT No.: PCT/DK86/00048
§ 371 Date: Mar. 7, 1988
§ 102(e) Date: Mar. 7, 1988
[87] PCT Pub. No.: WO87/07026
PCT Pub. Date: Nov. 19, 1987

[51] Int. Cl.⁴ .................. G01N 29/06; G01S 15/89
[52] U.S. Cl. ......................... 364/507; 73/618; 73/620
[58] Field of Search ............. 364/506, 507; 73/599, 73/600, 609, 614, 618, 619, 620–629

[56] References Cited

U.S. PATENT DOCUMENTS

| | | | |
|---|---|---|---|
| 3,673,860 | 7/1972 | Flaherty et al. | 73/620 |
| 3,857,052 | 12/1974 | Beller | 73/619 |
| 3,939,697 | 2/1976 | Lund et al. | 73/614 |
| 3,962,909 | 6/1976 | Lund | 73/620 X |
| 4,226,122 | 10/1980 | Lund et al. | 73/609 |
| 4,292,848 | 10/1981 | Rainey et al. | 73/602 |
| 4,481,822 | 11/1984 | Kubota et al. | 73/626 X |
| 4,495,816 | 1/1985 | Schlumberger | 73/600 |
| 4,531,409 | 7/1985 | Koch et al. | 73/588 |
| 4,597,292 | 7/1986 | Fujii et al. | 73/599 |
| 4,742,713 | 5/1988 | Abe et al. | 73/620 |

Primary Examiner—Felix D. Gruber
Attorney, Agent, or Firm—Banner, Birch, McKie & Beckett

[57] ABSTRACT

A computerized system for the recording of flaw images by ultrasonic examination according to the pulse-echo method includes at least one ultrasonic probe which can be moved in steps over the surface of an object along a rectilinear scanning path. Digital signals containing information on the successive positions of the sound beam, on echo amplitudes, and on the lengths of sound paths to reflectors inside the object, are processed and used for the accumulated storage of circular patterns of echo amplitude data in a matrix memory associated with a sectional plane through the object. A video screen terminal controls the system and transforms the accumulated data into displays of sectional flaw images of greatly improved precision and sharpness of definition. A gradual transfer of filtered data from a number of parallel sectional planes to three further matrix memories associated with projection planes at right angles to each other permits presentation in three dimensions of equally improved projection flaw images.

4 Claims, 2 Drawing Sheets

SYSTEM FOR ULTRASONIC EXAMINATION

BACKGROUND OF THE INVENTION

1. Field of the invention

This invention relates to the production and recording of inhomogeneities in otherwise homogeneous objects having a plane or locally substantially plane surface, by ultrasonic examination according to the pulse echo method. The production and recording of correct and well-defined images of internal inhomogeneities is a matter of the greatest importance for the correct location and sizing of internal flaws in materials and welded joints, and thus for the safety and fitness for purpose of important structures and installations.

2. Background of the Prior Art

In the ultrasonic examination art, great efforts have been made to develop improved systems for the location and sizing of flaws in materials and welded joints, in particular systems producing easily readable images of internal flaws. In many systems this has been made possible through the use of digital computing means including electronic matrix memories for the storage of echo data which may then be analysed, displayed on video monitors as grey scale or colour images, and permanently recorded by magnetic recording means or permanent prints.

Examples of extensive descriptions of ultrasonic examination systems of this kind for producing sectional views (B-scan displays) and plan views (C-scan displays) are Flathery U.S. Pat. No. 3,673,860 and Beller U.S. Pat. No. 3,857,052. Improved systems for the storage and display of complete projection images (P-scan displays) of flaws located in the interior of materials and welded joints have been described in Lund U.S. Pat. Nos. 3,939,697 and 4,226,122. However, none of the prior art examination systems have been entirely satisfactory.

The major and overriding problems in ultrasonic examination have not been associated with the ultrasonic equipment and techniques themselves, but with the complete and objective analysis and interpretation of the data, in particular the exact location and sizing of flaws. Small, but significant anomalies in the data are often overlooked, because the data is irregular and noisy, and the unavoidable beam spread of the ultrasonic sound beam leads to indistinct outlines of the flaw images.

SUMMARY OF THE INVENTION

The system according to the present invention has been evolved with the general object of overcoming the disadvantages of the prior art by providing sectional and projection views showing flaw images of hitherto unknown precision and sharpness of definition.

According to the invention, there is provided an examination system comprising at least one ultrasonic probe which can be moved over the surface of the object in steps of predetermined lengths along a rectilinear scanning path containing the projection on the surface of the central axis of the sound beam; position signal producing means adapted to produce digital signals containing information on the positions on said surface of the successive points of incidence of the sound beam; ultrasonic equipment adapted to make said probe emit, on completion of each step of movement, at least one short pulse of ultrasonic energy into the object, and adapted, on receipt of an echo pulse, to produce digital echo signals containing information on the amplitude of said pulse, and on the length of the sound path from said point of incidence to the reflecting point causing the echo pulse; digital computing means, including a first electronic matrix memory for data produced by the examination, said first matrix memory having storage addresses arranged in lines and columns associated with a similar, corresponding network of lines and columns of rectangular coordinates in the sectional plane through the object defined by the scanning path of the ultrasonic probe and the central axis of the sound beam, each storage address being adapted to store data representing said echo amplitudes, and adapted, on receipt of a new data item, to add said new data item to the sum of data items previously stored at said storage address; first control means for storing in said first matrix memory, upon receipt of said position signal and said echo pulse signals, data representing said echo amplitude at all storage addresses located on a circle, having as its centre the storage address associated with said point of incidence, and having as its radius the distance in said first matrix memory corresponding to said length of the sound path through the object; a video screen terminal for controlling the scanning movement of said ultrasonic probe, for controlling the functioning of said ultrasonic equipment, said digital computing means, and said first control means, and for displaying sectional images derived from data stored in said first matrix memory; recording means for producing permanent, electronically readable records of data stored in said first matrix memory, and of sectional images displayed on said screen terminal; and printing means for producing permanent prints of images displayed on said screen terminal.

Through this new and, in principle, quite simple storage system, echo amplitudes from significant flaws are drastically amplified due to the frequently repeated and accumulated storage of amplitude data at the same storage addresses, while the echo amplitudes of non-recurrent random noise signals remain substantially unamplified. At the same time, the effect of the beam spread of the sound beam is practically eliminated, because flaw echo amplitudes are no longer stored only at storage addresses associated with the central axis of the sound beam, but simultaneously at all storage addresses associated with the true path lengths, i.e. the true transit times measured for the individual echo pulses. When the accumulated sums of echo amplitude data items stored are displayed on the video screen in grey scale or colour presentations, it becomes possible to produce and record sectional flaw images (B-scan displays) of hitherto unknown precision and sharpness of definition.

According to the invention, an extended examination system may further be provided wherein said ultrasonic probe can be moved over the surface of the object along a number of successive, parallel rectilinear scanning paths at predetermined intervals; said digital computing means further includes a second electronic matrix memory for data produced by the examination, said second matrix memory having storage addresses arranged in lines and columns associated with a similar, corresponding network of lines and columns of rectangular coordinates in a projection plane parallel to the surface of the object, each storage address being adapted to store sums of data items representing said echo amplitudes; said digital computing means further includes second control means adapted, on completion of each movement of said ultrasonic probe along the length of a scanning path, to read from the storage addresses arranged in each column of said first matrix memory the highest sum of data items stored in said column, to store said highest sums of data at the corresponding storage addresses in said second matrix memory in the column associated with the line of intersection between said sectional plane and said projection plane, and to reset all storage addresses in said first matrix memory at zero value; said video screen terminal is further adapted to control the functioning of said second control means, and to display projection images derived from data stored in said second matrix memory; and said recording means is further adapted to produce permanent, electronically readable records of data stored in said second matrix memory.

Through this second storage, column by column, of the selected highest sums of echo amplitude data items obtained in a number of parallel sectional scannings, it becomes possible to produce and record projection flaw images (P-scan plan view displays) of hitherto unknown precision and sharpness of definition.

According to the invention, extended examination systems may further be provided, comprising the possibilities of producing similar projection flaw images on projection planes at right angles to the surface of the object and at right angles and/or parallel to the scanning paths for the ultrasonic probe. In this manner it becomes possible to produce and record improved further projection flaw images (P-scan side and end view displays), and thus to obtain a precise location and sizing of all internal inhomogeneities in three dimensions.

Other objects and advantages of the invention will be readily apparent from the following description taken in conjunction with the accompanying drawings.

DETAILED DESCRIPTION OF THE ILLUSTRATED EMBODIMENT

Figure 1:
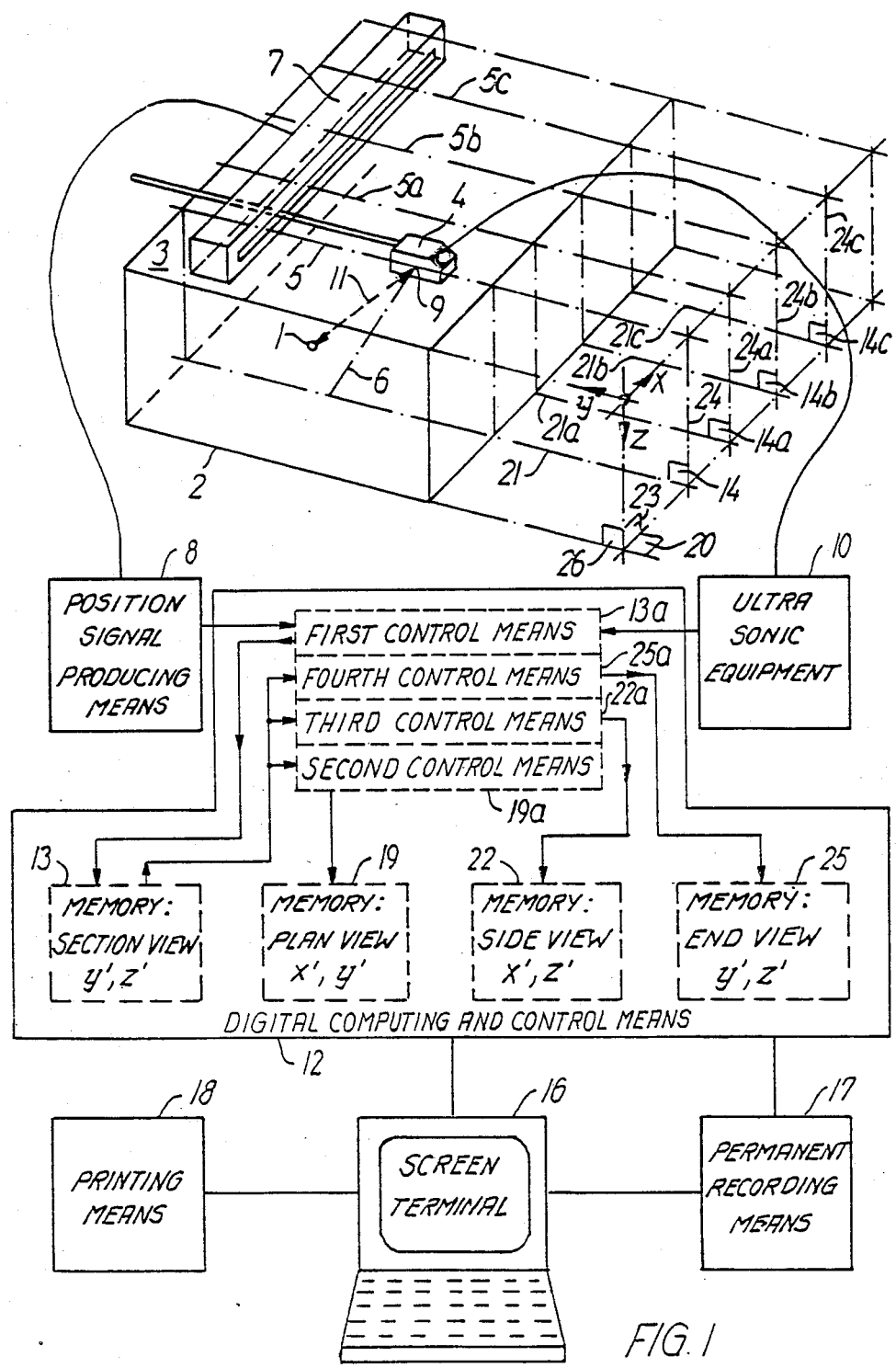
FIG. 1 is a schematic presentation, partly as an isometric view, and partly as a block diagram, of an inspection system according to the present invention.

FIG. 1 shows schematically an inspection system for producing and recording images of inhomogeneities 1 in an otherwise homogeneous object 2 having a plane surface 3. The system comprises an ultrasonic probe 4 which can be moved, manually or automatically, in steps of predetermined lengths along a rectilinear scanning path 5 containing the projection on the surface 3 of the central axis 6 of the sound beam emitted by the probe 4. Position signal producing means 7,8 including position transducers and analog-to-digital converting means, are adapted to produce and transmit digital signals containing information on the positions on the surface 3 of the successive points of incidence 9 of the sound beam. Ultrasonic equipment 10 is adapted to make the probe 4 emit, on completion of each step of movement, one or more short pulses of ultrasonic energy into the object 2, and, on receipt of an echo pulse, to produce and transmit digital echo signals containing information on the amplitude (a) of the echo pulse, and on the length of the sound path 11 from the point of incidence 9 to the reflecting inhomogeneity 1 causing the echo pulse.

Position and echo pulse signals are carried to digital computing and control means 12 including one or more electronic matrix memories 13, 19, 22, 25 for data produced by the examination. A video screen terminal 16 controls the scanning movement of the ultrasonic probe 4, controls the functioning of the ultrasonic equipment 10 and the digital computing and control means 12, and displays images derived from data stored in the matrix memories 13, 19, 22, 25. Recording means 17 is provided for producing permanent, electronically readable records of data stored in the matrix memories 13, 19, 22, 25, and of images displayed on the screen terminal 16. Printing means 18 is provided for producing permanent prints of images displayed on the screen terminal 16.

Figure 2:
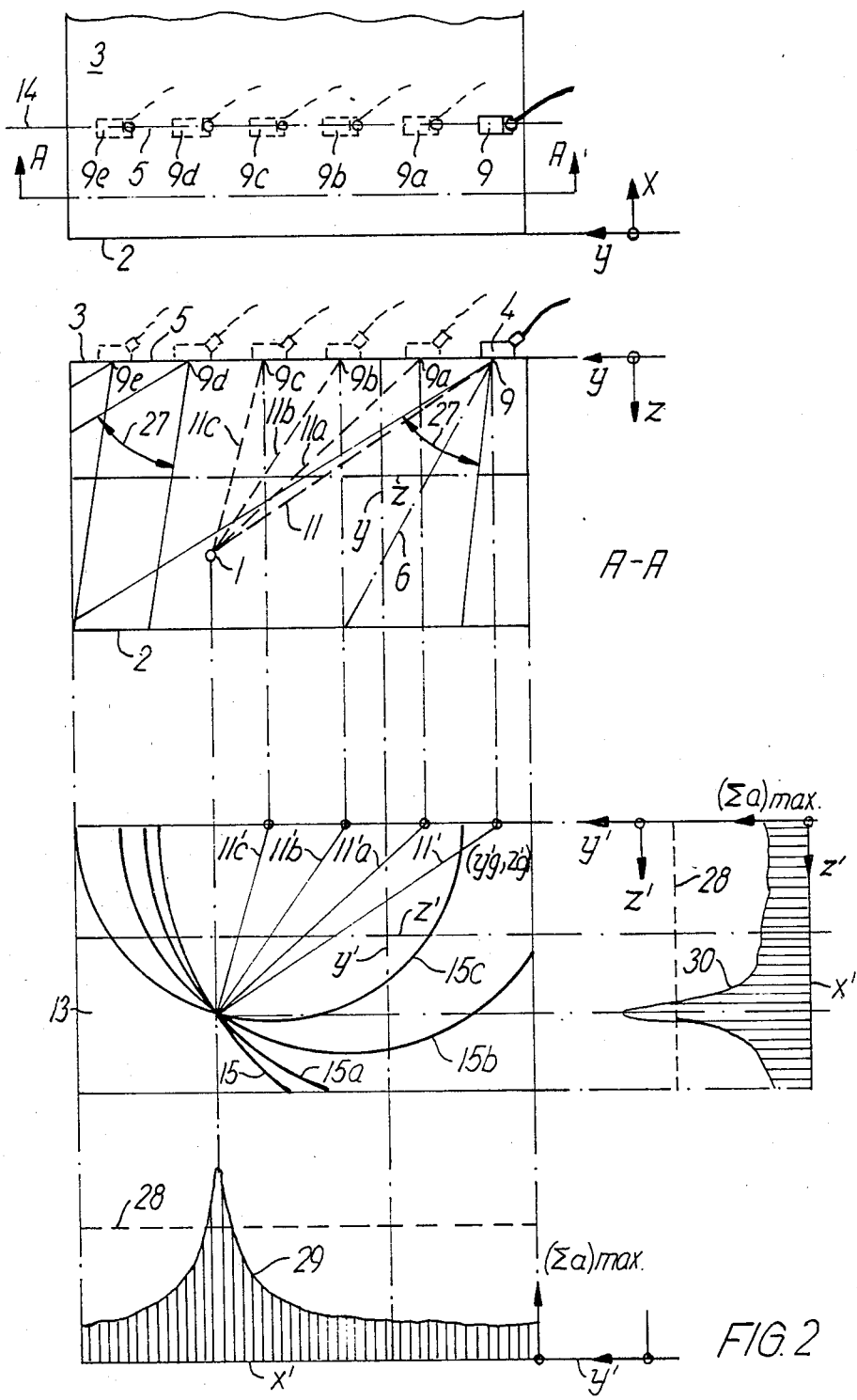
FIG. 2 is a schematic presentation of the production and storage of a sectional image (B-scan display) by means of the system of FIG. 1.

FIG. 2 further illustrates schematically the operation of the examination system when producing an image (B-scan display) of a sectional plane 14 through the object 2. The first matrix memory 13 has storage addresses $(y', z')$ arranged in lines $z'$ and columns $y'$ which are associated with a similar, corresponding network of lines z and columns y of rectangular coordinates (y, z) in the sectional plane 14 through the object defined by the scanning path 5 of the ultrasonic probe 4 and the central axis 6 of the sound beam. Each storage address $(y', z')$ is adapted to store data representing echo amplitudes (a), and adapted, on receipt of a new data item, to add the new data item (a) to the sum of data items (→a) previously stored at the same storage address.

First control means 13a included in the digital computing means 12 is adapted to arrange for the simultaneous storage in the first matrix memory 13, upon receipt of position and echo pulse signals, of data representing the echo amplitude (a) at all storage addresses $(y', z')$ located on a circle 15, having as its centre the storage address $(y'_9, z'_9)$ associated with the corresponding point of incidence 9 of the sound beam on the surface 3 of the object 2, and having as its radius the distance 11' in the matrix memory 13 which corresponds to the length of the sound path 11 from the point of incidence 9 to the reflecting inhomogeneity 1 inside the object.

The operation of the illustrated examination system is as follows. The ultrasonic probe 4 is mounted on the surface 3 of the object 2, placing the point of incidence 9 at the beginning of the scanning path 5, and arranging for the central axis 6 of the sound beam to be situated in the sectional plane 14 to be examined. The ultrasonic equipment 10 is then activated to let the probe 4 emit a short pulse of ultrasonic energy into the object. A reflecting inhomogeneity 1 within the opening angle 27 of the sound beam will then produce an echo pulse which is returned to the probe 4. The amplitude of the echo pulse depends on the nature and size of the reflector, and the transit time of the sound pulse is proportional to the length of the sound path 11. No information is obtained, however, about the angular position of the reflector within the sound beam, but this indefiniteness is neutralized to a great extent by the repeated storage at possible locations along a circle 15 in the matrix memory 13 as described above.

The probe 4 is then moved one step to the next position 9a, and the process described is repeated, resulting in the storage of a new data item at all storage addresses along the circle 15a, having as its radius the distance 11'a corresponding to the new sound path length 11a. The following steps to the positions 9b and 9c result in the storage of new data items along the circles 15b and 15c, having radii 11'b and 11'c corresponding to the path lengths 11b and 11c. After the fourth step to the position 9d, the reflector is outside the opening angle of the sound beam and thus no longer produces any echo pulse.

On completion of the scanning movement, the accumulated sums of data items ($\Sigma a$) in the matrix memory 13 can now be transformed into the display of a complete sectional image on the video screen of the terminal 16. This transformation may include one or more of several well-known techniques of digital image processing and image analysis, such as image filtering, contrast enhancement, grey scale or colour presentations, and the sectional image may be limited to include only stored sums of data items ($\Sigma a$) which are higher than an optional display limit 28.

The data stored in the first matrix memory 13 and the sectional images displayed may further be permanently recorded by the recording means 17 as electronically readable records that may be reinserted in the matrix memory 13 and redisplayed on the video screen for further analyses and comparisons at any later moment. The images displayed may further be copied in the form of permanent prints by the printing means 18.

It will be readily apparent from the above description that the examination system invented is able to produce flaw images of greatly improved precision and sharpness of definition. The accumulation of echo data items in the immediate vicinity of the intersections of the circles 15, 15a, 15b, 15c corresponding to the true position of the inhomogeneity 1 leads to a correspondingly increased contrast and sharpness of the flaw image, while the echo amplitudes of non-recurrent random noise signals remain substantially unamplified. The image quality obtained in this manner may be further improved by using smaller steps in the scanning movement of the probe 4, by using a finer network of storage addresses in the matrix memory 13, and by using a correspondingly greater number of pixels in the screen image of the terminal 16.

It will further be obvious to a person skilled in the art of ultrasonic examination with electronic data processing that it will be possible to construct a great number of suitable variants of the illustrated embodiment without deviating from the basic principles of the present invention.

The ultrasonic probe 4 may thus be an angle probe or a normal probe, and may suitably be replaced by a number of individual probes or by an array of ultrasonic transducers to be moved stepwise along the scanning path 5.

The echo signals may, for greater accuracy, be established as averaged values from a number of ultrasonic pulses emitted in each scanning position of the probe 4, and the digital data items to be stored in the matrix memory 13 may represent any suitable function of the echo amplitudes. One obvious choice would be to store and accumulate data items corresponding to the logarithmic values of the peak echo amplitudes, but other functions might be even more expedient considering the limitations in storage capacity at the individual storage addresses in the matrix memory 13.

The various components needed in the construction of an examination system as invented may by a person skilled in the art be chosen among a great number of currently available components for ultrasonic examinations, and for the production, processing, storage, display, and recording of digital data signals.

It will also be obvious that the system invented will be equally suitable for local examinations of objects having slightly curved surfaces, and for the examination of cylindrical objects such as tubes and pipes or pressure vessels, where the scanning paths may be chosen to be parallel to the axis of the cylindrical object.

According to the invention, the examination system may be extended to be able to produce equally improved projection flaw images on one or more projection planes 20, 23, 26 at right angles to each other as indicated schematically in FIG. 1. In this case the ultrasonic probe 4 is adapted to be moved over the surface 3 of the object 2 along a number of successive, parallel rectilinear scanning paths 5, 5a, 5b, 5c at predetermined intervals, and part of the sectional image data obtained in this manner is then used to constitute the data needed for producing projection images.

The digital computing means 12 then further includes a second electronic matrix memory 19 for data produced by the examination. The second memory 19 has storage addresses (x', y') arranged in lines y' and columns x' associated with a similar, corresponding network of lines y and columns x of rectangular coordinates (x, y) in a projection plane 20 parallel to the surface 3 of the object 2, and the storage addresses (x', y') are adapted to store sums of data items ($\Sigma a$) representing the echo amplitudes.

Second control means 19a included in the digital computing means 12 is adapted, on completion of each scanning movement of the probe 4 along the length of a scanning path 5, 5a, 5b, 5c, to read from the storage addresses (y', z') arranged in each column y' of the first matrix memory 13 the highest sum of data items $((\Sigma a)_{max})$ stored in said column y', and adapted to store these highest sums of data items $((\Sigma a)_{max})$ at the corresponding storage addresses (x', y') in the second matrix memory 19 in the column x' associated with the line of intersection 21, 21a, 21b, 21c between the sectional plane 14, 14a, 14b, 14c and the projection plane 20.

This data transfer has been indicated schematically in FIG. 2. The highest sums of data items $((\Sigma a)_{max})$ read from each column y' in the first memory 13 have been illustrated by the curve 29. The values illustrated by the curve 29 are then stored in the second matrix memory 19 along the corresponding column x' associated with the line of intersection 21 between the sectional plane 14 and the projection plane 20. Upon completion of this transfer, all storage addresses in the first memory 13 can, automatically or by order from the terminal 16, be reset at zero value in readiness for the storage of new data items resulting from the scanning of the following sectional plane 14a along the scanning path 5a.

In this manner the second matrix memory 19 is brought, column by column, to contain the accumulated data belonging to an image projected on to the projection plane 20. Upon completion of the entire scanning procedure, the accumulated data can be transferred into the display on the video screen of the terminal 16 of a complete projection image (P-scan plan view) of greatly improved precision and sharpness of definition. The data stored in the second matrix memory 19 and the projection images displayed may be permanently recorded by the recording means 17, and the images displayed may be copied in the form of permanent prints by the printing means 18.

According to the invention, the examination system may be extended in a quite similar manner to be able to produce improved projection flaw images on a projection plane 23 at right angles to the surface 3 of the object 2, and at right angles to the scanning paths 5, 5a, 5b; 5c of the probe 4.

In this case the digital computing means further includes a third electronic matrix memory 22 for data produced by the examination. This third memory 22 has storage addresses (x', z') arranged in lines z' and columns x' associated with a similar, corresponding network of lines z and columns x of rectangular coordinates in the projection plane 23, and the storage addresses (x', z') are adapted to store sums of data items ($\Sigma a$) representing the echo amplitudes.

Third control means 22a included in the digital computing means 12 is adapted, on completion of each scanning movement of the probe 4 along the length of a scanning path 5, 5a, 5b, 5c, to read from the storage addresses (y', z') arranged in each line z' of the first matrix memory 13 the highest sum of data items $((\Sigma a)_{max})$ stored in said line z', and adapted to store these highest sums of data items $((\Sigma a)_{max})$ at the corresponding storage addresses (x', z') in the third matrix memory 22 in the column x' associated with the line of intersection 24, 24a, 24b, 24c between the sectional plane 14, 14a, 14b, 14c and the projection plane 23.

This data transfer has been indicated schematically in FIG. 2. The highest sums of data items max $((\Sigma a)_{max})$ read from each line z' in the first memory 13 have been illustrated by the curve 30. The values illustrated by the curve 30 are then stored in the third matrix memory 22 along the corresponding column x' associated with the line of intersection 24 between the sectional plane 14 and the projection plane 23. Upon completion of the two data transfers from memory 13 to memories 19 and 22, all storage addresses in the first memory 13 can, automatically or by order from the terminal 16, be reset at zero value in readiness for the storage of new data items resulting from the scanning of the following sectional plane 14a along the scanning path 5a.

In this manner the third matrix memory 22 is brought, column by column, to contain the accumulated data belonging to an image projected on to the projection plane 23. Upon completion of the entire scanning procedure, the accumulated data can be transformed into the display on the video screen of the terminal 16 of a complete projection image (P-scan side view) of greatly improved precision and sharpness of definition. The data stored in the third matrix memory 22 and the projection images displayed may be permanently recorded by the recording means 17, and the images displayed may be copied in the form of permanent prints by the printing means 18.

According to the invention the examination system may finally be extended to be able to produce improved flaw images on a projection plane 26 at right angles to the surface 3 of the object 2, and parallel to the scanning paths 5, 5a, 5b, 5c of the probe 4.

In this case the digital computing means 12 further includes a fourth electronic matrix memory 25 for data produced by the examination. This fourth matrix memory 25 has storage addresses (y', z') arranged in lines z' and columns y' associated with a similar, corresponding network of lines z and columns y of rectangular coordinates (y, z) in the projection plane 26, and the storage addresses (y', z') are adapted to store sums of data items ($\Sigma a$) representing the echo amplitudes.

Fourth control means 25a included in the digital computing means is adapted, on completion of each scanning movement of the probe 4 along the length of a scanning path 5, 5a, 5b, 5c, to read from each storage address (y', z') in the first matrix memory 13 the sum of data items ($\Sigma a$) stored at said address (y', z'), and to store said sum of data items ($\Sigma a$) at the corresponding address (y', z') in the fourth matrix memory 25, but only if a higher sum of data items has not already been stored at the storage address in question. Upon completion of the three data transfers from memory 13 to memories 19, 22 and 25, all storage addresses in the first memory 13 can, automatically or by order from the terminal 16, be reset at zero value in readiness for the storage of new data items resulting from the scanning of the following sectional plane 14a along the scanning path 5a.

In this manner the fourth matrix memory 25 is brought, transfer by transfer, to contain the accumulated data belonging to an image projected on to the projection plane 26. Upon completion of the entire scanning procedure, the accumulated data can be transformed into the display on the video screen of the terminal 16 of a complete projection image (P-scan end view) of greatly improved precision and sharpness of definition. The data stored in the fourth matrix memory 25 and the projection images displayed may be permanently recorded by the recording means 17, and the image displayed may be copied in the form of permanent prints by the printing means 18.

The three projection images may, like the sectional images, be subjected to digital image processing and image analysis, such as image filtering, contrast enhancement, grey scale or colour presentations, and the projection images may be limited to include only stored sums of data items ($\Sigma a$) which are higher than an optional display level 28. The image quality obtained may be further improved by using smaller intervals between the scanning paths 5, 5a, 5b, 5c of the probe 4, by using a finer network of storage addresses in the matrix memories 13, 19, 22, 25, and by using a correspondingly greater number of pixels in the screen image of the terminal 16.

During an automatic examination of an object, the operator may follow the gradual build-up of sectional and/or projection images on the screen of the terminal 16, and may interrupt the scanning procedure before the automatic erasing of a sectional image of particular interest. In this manner he is able to make permanent records and prints of particularly interesting sectional images, before continuing the automatic examination and re-use of the first matrix memory 13. This feature emphasizes another aspect of the superiority of the invented system in relation to prior art.

In prior art it has been necessary, in order to obtain comparably high-quality sectional and projection images, to store position and echo pulse signals from every small element of the entire volume of the object examined, and to subject this vast amount of data to comprehensive and complicated mathematical analysis and processing. This again requires the application of very considerable computing power and magnetic storage and recording capacity, and the equipment needed consequently becomes expensive, bulky, heavy, and complicated in practical use. In comparison, the invented system requires only small computing power and storage and recording capacity, and can easily be combined into one lightweight, hand-portable unit which is quite simple to operate in practical use.

It will be understood that several modifications and variations of the described systems may be effected without departing from the spirit and scope of the novel concept of the present invention.

We claim:

1. A system for producing and recording images of inhomogeneities in otherwise homogeneous objects having a plane or locally substantially plane surface, by ultrasonic examination according to the pulse-echo method, wherein at least one ultrasonic probe can be moved over the surface of the object in steps of predetermined lengths along a rectilinear scanning path containing the projection on the surface of the central axis of the sound beam, position signal producing means produces digital signals containing information on the position on said surface of the successive points of incidence of the sound beam, ultrasonic equipment makes said probe emit, on completion of each step of movement, at least one short pulse of ultrasonic energy into the object, and produces, on receipt of an echo pulse, digital signals containing information on the amplitude of said echo pulse, and on the length of the sound path from said point of incidence to the reflecting point causing the echo pulse, digital computing means, including a first electronic matrix memory for data produced by the examination, said first matrix memory having storage addresses arranged in lines and columns associated with a similar, corresponding network of lines and columns of rectangular coordinates in the sectional plane through the object defined by the scanning path of the ultrasonic probe and the central axis of the sound beam, stores at each storage address data representing said echo amplitudes, and adds, on receipt of a new data item, said new data item to the sum of data items previously stored at said storage address, first control means stores in said first matrix memory, upon receipt of said position signals and said echo pulse signals, data representing said echo amplitudes at all storage addresses located on a circle, having as its center the storage address associated with said point of incidence, and having as its radius the distance in said first matrix memory corresponding to said length of the sound path through the object, a video screen terminal controls the scanning movement of said ultrasonic probe, controls the functioning of said ultrasonic equipment, said digital computing means, and said first control means, and displays sectional images derived from data stored in said first matrix memory, recording means produces permanent, electronically readable records of data stored in said first matrix memory, and of sectional images displayed on said screen terminal, printing means produces permanent prints of images displayed on said screen terminal, said ultrasonic probe can be moved over the surface of the object along a number of successive, parallel rectilinear scanning paths at predetermined intervals, said digital computing means further includes a second electronic matrix memory for data produced by the examination, said second matrix memory having storage addresses arranged in lines and columns associated with a similar, corresponding network of lines and columns of rectangular coordinates in a projection plane parallel to the surface of the object, where each storage address stores sums of data items representing said echo amplitudes, characterized in that:

said digital computing means further includes second control means which, on completion of each movement of said ultrasonic probe along the length of a scanning path, reads from the storage addresses arranged in each column of said first matrix memory the highest sum of data items stored in said column, stores said highest sums of data items at the corresponding storage addresses in said second matrix memory in the column associated with the line of intersection between said sectional plane and said projection plane, and resets all storage addresses in said first matrix memory at zero value;

said video screen terminal further controls the functioning of said second control means, and displays projection images derived from data stored in said second matrix memory; and said recording means further produces permanent electronically readable records of data stored in said second matrix memory.

2. The system of claim 1, wherein said digital computing means further includes a third electronic matrix memory for data produced by the examination, said third matrix memory having storage addresses arranged in lines and columns associated with a similar, corresponding network of lines and columns of rectangular coordinates in a projection plane at right angles to said scanning paths, where each storage address stores sums of data items representing said echo amplitudes, characterized in that:

said digital computing means further includes third control means which, on completion of each movement of said ultrasonic probe along the length of a scanning path, reads from the storage addresses arranged in each line of said first matrix memory the highest sum of data items stored in said line, stores said highest sums of data items at the corresponding storage addresses in said third matrix memory in the column associated with the line of intersection between said sectional plane and said projection plane, and resets all storage addresses in said first matrix memory at zero value;

said video screen terminal further controls the functioning of said third control means, and displays projection images derived from data stored in said third matrix memory; and said recording means further produces permanent, electronically readable records of data stored in said third matrix memory.

3. The system of claim 2, wherein said digital computing means further includes a fourth electronic matrix memory for data produced by the examination, said fourth matrix memory having storage addresses arranged in lines and columns associated with a similar, corresponding network of rectilinear coordinates in a projection plane at right angles to the surface of the object and parallel to said scanning paths, where each storage address stores sums of data items representing said amplitudes, characterized in that:

said digital computing means further includes fourth control means which, on completion of each movement of said ultrasonic probe along the length of a scanning path, reads from each storage address in said first matrix memory the sum of data items stored at said address, stores said sum of data items at the corresponding storage address in said fourth matrix memory, but only if a higher sum of data items has not already been stored at the storage address in question, and resets all storage addresses in said first matrix memory at zero value;

said video screen terminal further controls the functioning of said fourth control means, and displays projection images derived from data stored in said fourth matrix memory; and said recording means further produces permanent, electronically readable records of data stored in said fourth matrix memory.

4. The system of claim 1, wherein said digital computing means further includes a fourth electronic matrix memory for data produced by the examination, said fourth matrix memory having storage addresses arranged in lines and columns associated with a similar, corresponding network of rectilinear coordinates in a projection plane at right angles to the surface of the object and parallel to said scanning paths, where each storage address stores sums of data items representing said echo amplitudes, characterized in that:

said digital computing means further includes fourth control means which, on completion of each movement of said ultrasonic probe along the length of a scanning path, reads from each storage address in said first matrix memory the sum of data items stored at said address, stores said sum of data items at the corresponding storage address in said fourth matrix memory, but only if a higher sum of data items has not already been stored at the storage address in question, and resets all storage addresses in said first matrix memory at zero value;

said video screen terminal further controls the functioning of said fourth control means, and displays projection images derived from data stored in said said fourth matrix memory; and said recording means further produces permanent, electronically readable records of data stored in said fourth matrix memory.

* * * * *